United States Patent [19]
Endres

[11] 3,979,463
[45] Sept. 7, 1976

[54] FLUOROALIPHATIC PHENOLS

[75] Inventor: Leland S. Endres, San Luis Obispo, Calif.

[73] Assignee: Minnesota Mining and Manufacturing Company, St. Paul, Minn.

[22] Filed: Mar. 18, 1974

[21] Appl. No.: 451,920

Related U.S. Application Data

[63] Continuation of Ser. No. 84,508, Oct. 27, 1970, abandoned.

[52] U.S. Cl. .................... 260/623 D; 260/619 R; 260/612 D; 260/613 D; 260/625; 260/621 R; 106/2; 424/45; 424/346; 424/358
[51] Int. Cl.² ........................................ C07C 39/26
[58] Field of Search ........ 260/623 D, 623 R, 648 F, 260/649 R, 621 R, 619 R, 624, 625, 612 D, 613 D

[56] References Cited
UNITED STATES PATENTS 2,811,566  10/1957  Bader ............................. 260/623 D
2,965,659  12/1960  Tier ................................. 260/408

Primary Examiner—James O. Thomas, Jr.
Assistant Examiner—W. B. Lone
Attorney, Agent, or Firm—Alexander, Sell, Steldt & DeLaHunt

[57] ABSTRACT

Fluoroaliphatic phenols are prepared by reacting an olefinic phenol with a perfluoroalkyl sulfonyl chloride, bromide, or fluoride in the presence of a free radical catalyst at a temperature of from about 100°–150° C. The fluoroaliphatic phenols are useful in the preparation of condensation products with aldehydes which products are substantive to the skin and render the skin or similar materials repellent to aqueous and oily materials.

7 Claims, No Drawings

FLUOROALIPHATIC PHENOLS

This is a continuation of application Ser. No. 84,508 filed Oct. 27, 1970 now abandoned.

BACKGROUND OF THE INVENTION

The present invention relates to novel fluoroaliphatic phenols and their method of preparation. More particularly, the present invention relates to fluoroaliphatic phenols which form condensation products with certain aldehydes can be prepared, which products are adapted to topical application to provide the skin with protection which is not readily removed by mild abrasion or hot detergents.

At present, lotions, creams, and various other emollient compositions are intended to exert a beautifying, softening and lubricating effect on the skin and may even contain medicinal ingredients. However, these preparations, quite effective to some degree, all suffer from certain disadvantages. Mere emollients fail to protect the skin from exposure to injurious materials and only serves palliative remedies afterwards. Barrier creams have been useful for certain specific conditions, but heretofore have failed to have broad general applicability. Furthermore, in maintaining personal hygiene, such as washing the hands, compositions of the prior art are largely removed and repeated applications are necessary.

To provide skin-protective compositions that resist removal from the skin by washing, particular ingredients have been incorporated into various compositions. For example, U.S. Pat. No. 2,727,846 teaches the incorporation of siloxanes into skin protective compositions. Such compositions, however, are easily transferred from the hands by touch or slight abrasion with other materials.

To overcome the disadvantages of siloxane-containing skin-protective compositions, it has been proposed (i.e., U.S. Pat. No. 3,100,180) that the siloxane can be replaced by a minor amount of fluorocarbon elastomer. In U.S. Pat. No. 3,470,292, it was proposed that the disadvantage of siloxane in skin-protective compositions could be overcome by incorporating a phosphatide, such as lecithim, kephalin, and sphingomyelin.

Certain phenols have been described in the art. For example, Beilstein, *Organische Chemie*, Vol. VIII, p. 102 (1925) and in Mattson, U.S. Pat. No. 3,326,928. These phenols, although useful in the preparation of protective materials, are not generally preferred for all applications.

SUMMARY OF THE INVENTION

According to the present invention there are provided novel fluoroaliphatic phenols prepared by reacting a olefinic phenol with a perfluoroalkyl sulfonyl chloride, bromide or fluoride in the presence of a free radical catalyst. The novel fluoroaliphatic phenols of the instant invention are useful in preparing protective compositions for the skin. The compositions are useful in the prevention of "dish-pan hands" caused by repeated immersion of the hands in hot water containing soap or detergents. These protective compositions comprise generally a condensation product of the novel phenols of the instant invention and a suitable aldehyde. Such an aldehyde-phenol condensation product is generally referred to in the art as a "novolak". The condensation products are substantive to human and animal skin and, by reason of this substantivity, afford long-lasting protection of the skin to water and oil.

According to the present invention, the novel perfluoroalkyl compounds have, generally, the formula

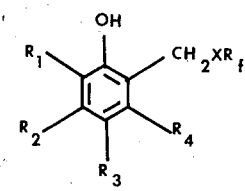

wherein X is —CHClCH$_2$—, —CH=CH— or —CH$_2$—CH$_2$—; R$_f$ is a perfluoroalkyl having from 3 to 20 carbon atoms; any of R$_1$, R$_2$, R$_3$ and R$_4$ are methyl, ethyl, methoxy, phenyl, phenoxy, hydroxy, hydrogen, halogen and any two adjacent R groups can form carbocyclic and heterocyclic rings; and R$_1$ and R$_3$ can be —CH$_2$XR$_f$.

The fluoroaliphatic phenols of the present invention are prepared, generally, by a. reacting an olefinic phenol, having its hydroxyl group protected by suitable substituent or moiety, with a perfluoroalkyl sulfonyl chloride (ClSO$_2$R$_f$) in the presence of a free radical catalyst;

b. hydrolyzing the product formed in step (a); and c. isolating the product.

The preferred olefinic phenol is allylphenyl acetate and has the following formula:

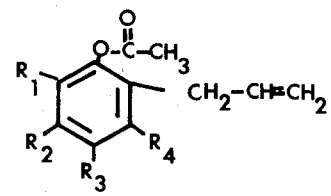

wherein any of R$_1$, R$_2$, R$_3$ and R$_4$ are methyl, ethyl, methoxy, phenyl, phenoxy, hydroxy, hydrogen, halogen and any two adjacent R groups can form carbocyclic and heterocyclic rings; and R$_1$ and R$_3$ can be —CH$_2$XR$_f$.

In the preferred method, the reaction is carried out at a temperature of from about 80°–150° C. for about 15 minutes to 1 hour. The preferred temperature is about 120°–140° C. and the preferred time of reaction is about 30 minutes.

Examples of fluoroaliphatic phenols prepared according to the present invention and useful in the preparation of substantive lotions and creams are as follows:

Table I

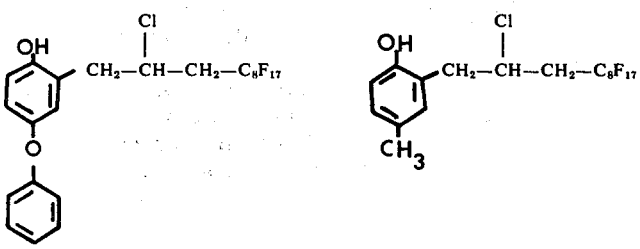

Table I-continued

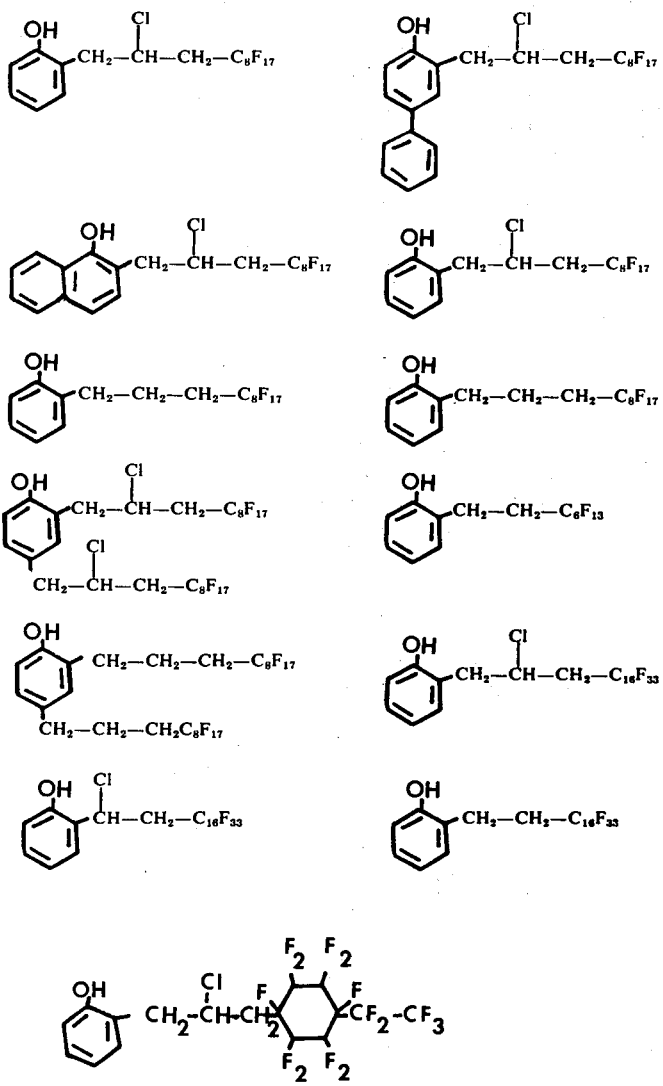

As heretofore noted, the skin may be both oleophobic and resistant to aqueous materials, including acids and bases, and also protected from irritating and otherwise undesirable substances, by applying thereto compositions comprising certain aldehyde condensation products of the novel fluoroaliphatic phenols of the instant invention, the condensation product being extended in a suitable pharmaceutical media.

The term "substantive" as used herein, means that the materials has a high degree of tenacity for the skin and is essentially non-removable by normal procedures. It is believed, though applicants do not intend to be bound thereby, that the condensation products as described herein are actually chemically bound to the skin at least to some extent. Compositions useful for the purpose of the present invention are provided by incorporating a minor amount of aldehyde condensation product of the instant fluoroaliphatic phenols into a major amount of an aqueous pharmaceutically acceptable extending medium of the aqueous emulsion type which may also contain a thixotropic bodying agent or thickening agent. Preferably, there is employed from about 0.3 to about 20% by weight of the condensation product. The term "pharmaceutical extending medium" as used herein, includes such preparations as the basis for lotions, creams, ointments, and the like and water-based preparations for topical application, which are sufficiently bodied so that the resultant composition is not watery or thin, though without limiting the viscosity of compositions only to a single type of preparation.

The aldehyde condensation products of the fluoroaliphatic phenols of the instant invention that are preferred are the acid catalyzed reaction products of the aldehyde and the instant fluoroaliphatic phenols.

The aldehyde useful in the preparation of the condensation products has the formula

RCHO wherein R is hydrogen or an organic radical having not more than 7 carbon atoms, and which may be substituted by methyl, methoxy, ethyl, or ethoxy groups. More preferably, R is a lower alkyl group of the class $C_nH_{2n+1}$, wherein $n$ is an integer of from 1 to 4. The aldehyde may be introduced into the reaction mixture either as a monomeric material or as the equivalent polymeric material which is convertible under condensation conditions to monomeric aldehydes.

Examples of aldehydes which are useful for purposes of the present invention are cetyl aldehyde, benzaldehyde, peraldehyde and trioxane. The preferred aldehyde is formaldehyde.

The pharmaceutical extending medium consists of all the various ingredients and adjuvants normally employed as a base except for the formaldehyde condensation product of the perfluoroalkyl phenols which are added as an alcoholic solution or aqueous dispersion. Illustrative of the types of materials which can be incorporated optionally in desired amounts for particular purposes are humectants, therapeutic ingredients, perfumes and colorants.

Catalysts which may be used herein are acid or base catalysts. Strong acids, such as sulfonic acids (sulfuric acid) or weak acids such as halogenated aliphatic acids (acetic acid) may be used to prepare the condensation products. Preferred acids are trichloroacetic and para-toluene sulfonic acids. Of the many alkaline catalysts which may be used to prepare the condensation products, sodium hydroxide is preferred. Other catalysts include bases such as the hydroxide oxides and carbonates of lithium, sodium, potassium, cesium, magnesium, calcium, strontium, barium, and zinc oxide.

As with most phenol aldehyde condensation reactions, the character of the product obtained is very dependent upon component reactivity, concentration and reaction conditions. In general, condensation products of the fluoroaliphatic phenols of the instant invention are higher in molecular weight and hardness where the catalyst is very active, catalyst concentration is high, the aldehyde concentration is high and the reaction temperature is high. In general, the effectiveness of acid catalyst decreases as follows: hydrochloric, nitric, sulfuric, trichloroacetic, oxalic, phosphoric, dichloroacetic, chloroacetic, formic, lactic, and acetic. Also, the more reactive the phenol and aldehyde, the higher the molecular weight and hardness of the condensation product obtained.

Desirable condensation products are prepared using mole ratios of fluoroaliphatic phenols to aldehyde of about 1.1:0.3 to 1.0:3.5 or more. The preferred fluoroaliphatic phenol to aldehyde ratio is 1.0:0.6 to 1.0:1.3. Reaction temperatures that may be used are from about 40° to about 150° C. or higher and the preferred reaction temperatures are from about 80° to about 110° C.

The lower molecular weight condensation products, in general, are soft waxes having a buttery consistency. The condensation products prepared from 2-(2'-chloro-3'-perfluorooctyl)-n-propyl phenol and formaldehyde, have an average molecular weight of about 800 to about 1500 and are soft primarily because they are not a precise reaction product but are mixtures of reaction products including unreacted phenol, phenol acted with 1 or more aldehyde molecules, 2 phenol moieties reacted with 1 or more aldehydes, etc. These products possess the greatest amount of substantivity to skin, leather, wool and polyamide surfaces.

The present invention will be more clearly understood with reference to the following, non-limiting examples wherein all parts are by weight unless otherwise specified.

EXAMPLE 1

Preparation of 2-(2'-chloro-3'-perfluorooctyl)-n-propyl phenol

A 2-liter 3-neck flask equipped with a mechanical stirrer, a sparger tube and means for absorbing sulfur dioxide, and means for heating the flask, was charged with 225.6 grams of 2-allylphenyl acetate (1.45 moles) and heated to 120° C. When the temperature reached 120° C., there was added 0.2 grams of benzoyl peroxide and, over a period of 2 hours, 755 grams (1.45 moles) of perfluorooctane sulfonyl chloride (b.p. 194° C.; $n_D^{25}$ 1.3200) was added while maintaining the temperature at 120° to 140° C. To maintain a concentration of free radicals in the reaction mixture, there was added periodically during the 2 hours small portions of additional benzoyl peroxide (a total of 1.0 grams including the initial 0.2 grams were added). The mixture was heated at 120° an additional 30 minutes after the addition was complete. Then, without cooling, the flask was rigged for vacuum distillation. Vacuum was applied cautiously to avoid foaming and the mixture distilled. There was obtained 729.2 grams of 2-(2'-chloro-3'-perfluorooctyl-n-propyl) phenyl acetate (79.7% conversion) b.p. 140° C./0.40 mm. and unreacted o-allylphenyl acetate. This compound is the precursor for the corresponding phenol.

Into a 10-liter flask equipped with a 2-foot diltillation column and fractionation take-off head and means for heating the flask was placed 729.2 grams (1.16 moles) of 2-(2'-chloro-3'-perfluorooctyl)-n-propyl phenyl acetate, 7 liters of absolute alcohol and 1.0 gram of p-toluene sulfonic acid. The mixture was heated to reflux and over a period of 8 hours after which 4 liters of ethanol were removed by distillation. Of samples taken from the flask during this time, there was an indication of a continued decrease in acetate group contant as determined by infrared analysis. Distillation was continued to remove the remaining ethanol. The residue in the flask was purified by absorption on silica gel and elution with an 80:20 benzene:hexane solution. After removal of the solvent by distillation, taking care not to overheat the product, 637.9 grams of 2-(2'-chloro-3'-perfluorooctyl)-n-propyl phenol was obtained (99.5% of the theoretical amount). Melting point 69°–73° C. Analysis: Calculated for $C_{17}H_{10}ClF_{17}O$; C, 34.7%; H, 1.7%; 1, 0.7%; F, 54.9%. Found; C, 34.6%; H, 0; 1, 1.79%; F, 54.8%. The above reactions are believed to be properly represented as follows:

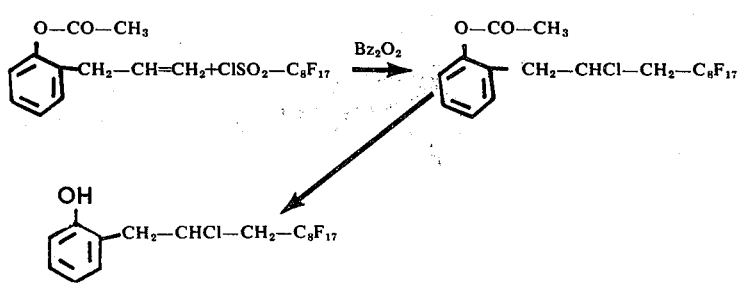

EXAMPLE 2

By performing the procedures of Example 1, using in place of 2-allylphenyl acetate an isomeric mixture of 3- and 5-chloro-2-allyl phenyl acetates, the isomeric mixture of 3- and 5-chloro-2-(2'-chloro-3'-perfluorooctyl)-n-propyl phenyl acetate (b.p. 153° C./0.6 mm.) was prepared from which the isomeric mixture of 3- and 5-chloro-2-(2'-chloro-3'-perfluorooctyl)-n-propyl phenols (yellow wax-like material may be prepared. Analysis: Calculated for $C_{17}H_9Cl_2F_{17}O$; C, 32.8%; H, 1.4%; F, 51.8%. Found; C, 33.2%; H, 1.6%; F, 51.8%.

EXAMPLE 3

When an isomeric mixture of 3- and 5-methyl-2-allyl phenyl acetates is carried through according to the procedures set out in Example 1 in place of 2-allylphenyl acetate, the isomeric mixture of 3- and 5-methyl-2-(2'-chloro-3'-perfluorooctyl)-n-propyl phenyl acetate was prepared (b.p. 150° C./0.40 mm.) from which the isomeric mixture of 3- and 5-methyl-2-(2'-chloro-3'-perfluorooctyl)-n-propyl phenols (wax-like material) was prepared. Analysis: Calculated for $C_{18}H_{12}ClF_{17}O$; C, 35.8%; H, 2.0%; F, 53.7%; Found; C, 35.8%; H, 2.1%; F, 53.8%.

EXAMPLE 4

Additional ω-perfluoroalkyl-propyl phenyl acetate and the phenols may be prepared therefrom, are given in Table II.

TABLE II

| ω-Perfluoroalkyl-Propyl Acetate | Corresponding ω-Perfluoroalkyl-Propyl Phenol |
|---|---|
| 4-chloro-2-(2'-chloro-3'-perfluorooctyl)-n-propyl phenyl acetate (b.p. 150°C/0.15 mm) | 4-chloro-2-(2'-chloro-3'-perfluorooctyl)-n-propyl phenol (m.p. 88–93° C.) |
| 3,4,6-trichloro-2-(2'-chloro-3'-perfluoro-octyl)-n-propyl phenyl acetate (b.p. 147°C/0.07 mm) | 3,4,6-trichloro-2-(2'-chloro-3'-perfluorooctyl)-n-propyl phenyl (m.p. 84–88° C.) |
| 2,6-dichloro-3-(2'-chloro-3'-perfluorooctyl)-n-propyl phenyl acetate (b.p. 160°C/0.05 mm) | 2,6-dichloro-3-(2'-chloro-3'-perfluorooctyl)-n-propyl phenol (m.p. 88–89° C.) |
| Isomeric mixture of 2,4- and 2,6-diacetoxy-1-(2'-chloro-3'-perfluorooctyl)-n-propyl benzene (b.p. 170°C/0.1 mm) | Isomeric mixture of 2,4- and 2,6-dihydroxy-1-(2'-chloro-3'-perfluorooctyl-n-propyl benzene |

The ω-perfluoroalkyl-propyl acetates of Table II were prepared from 4-chloro-2-allyl-phenyl acetate, 3,4,6-tri-chloro-2-allyl-phenyl acetate, 2,6-dichloro-3-allyl-phenyl acetate and an isomeric mixture of 2,4- and 2,6-diacetoxy-allyl-phenyl acetate respectively.

EXAMPLE 5

Table III gives the structure of yet other alkenylphenyl acetates that may be used to prepare additional ω-perfluoroalkyl-phenols of this invention. These compounds also may be prepared by following the processes of Example 1 using appropriate properties of ω-perfluoro-alkyl sulfonyl halide and alkenyl phenyl acetate.

TABLE III

| Alkenyl Phenyl Acetates | Perfluoroalkyl Sulfonyl Halide | ω-Perfluoroalkyl Alkyl Phenol |
|---|---|---|
| 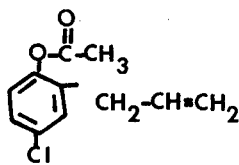 |  $C_4F_9SO_2Cl$ | 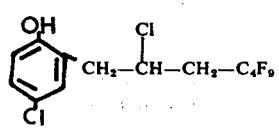 |
| 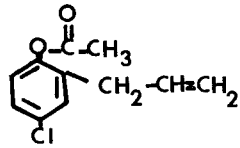 |  $C_6F_{13}SO_2Cl$ | 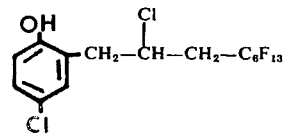 |

TABLE III-continued

| Alkenyl Phenyl Acetates | Perfluoroalkyl Sulfonyl Halide | ω-Perfluoroalkyl Alkyl Phenol |
|---|---|---|
| 4-Cl, 2-allyl phenyl acetate | $C_8F_{17}SO_2Cl$ | 4-Cl, 2-(2-chloro-perfluoroalkyl propyl) phenol |
| 4-Cl, 2-allyl phenyl acetate | $C_{12}F_{25}SO_2Cl$ | 4-Cl, 2-(2-chloro-perfluoroalkyl propyl) phenol |
| 4-Cl, 2-allyl phenyl acetate | $C_{20}F_{41}SO_2Cl$ | 4-CH₃, 2-(2-chloro-perfluoroalkyl propyl) phenol |
| 4-CH₃, 2-allyl phenyl acetate | $C_8F_{17}SO_2Cl$ | 4-CH₃, 2-(2-chloro-perfluoroalkyl propyl) phenol |
| 4-phenyl, 2-allyl phenyl acetate | $C_8F_{17}SO_2Cl$ | 4-phenyl, 2-(2-chloro-perfluoroalkyl propyl) phenol |
| 4-Br, 2-allyl phenyl acetate | $C_8F_{17}SO_2Cl$ | 4-Br, 2-(2-chloro-perfluoroalkyl propyl) phenol |
| 2-vinyl phenyl acetate | $C_8F_{17}SO_2Cl$ | 2-(1-chloro-perfluoroalkyl ethyl) phenol |
| 2-vinyl phenyl acetate | $C_8F_{17}SO_2Cl$ | bis-phenol product |
| 4-OCH₃, 2-allyl phenyl acetate | $C_{12}F_{25}SO_2Cl$ | 4-OCH₃, 2-(2-chloro-perfluoroalkyl propyl) phenol |

(Note: Structures shown in image; chemical names are descriptive approximations of the drawn structures.)

TABLE III-continued

| Alkenyl Phenyl Acetates | Perfluoroalkyl Sulfonyl Halide | ω-Perfluoroalkyl Alkyl Phenol |
|---|---|---|
| 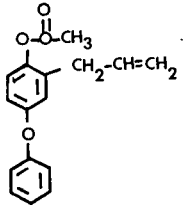 | $C_{12}F_{25}SO_2Cl$ | 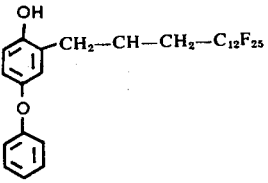 |
| 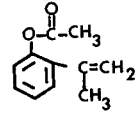 | $C_8F_{17}SO_2Cl$ | 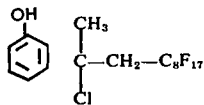 |
| 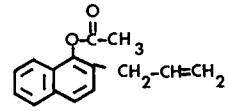 | $C_8F_{17}SO_2Cl$ | 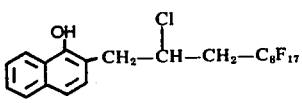 |
| 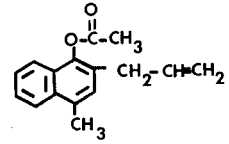 | $C_8F_{17}SO_2Cl$ | 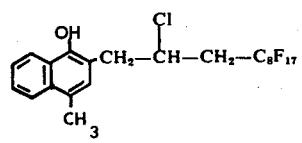 |
| 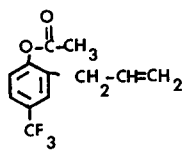 | $C_6F_{13}SO_2Cl$ | 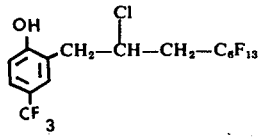 |
| 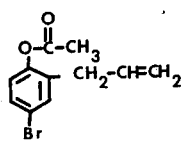 | $C_4F_9SO_2Cl$ | 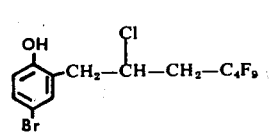 |

The alkenyl-phenyl acetates of Table III and those used in Examples 1 and 2 are prepared from the alkenyl-phenyl ethers which in turn are prepared from the phenols and alkenyl bromides. These reactions are well known procedures. See: J. Am. Chem. Soc., 72, 839–41 (1950); J. Org. Chem. 19, 726–32 (1956); J. Chem. Soc., Japan 57, 599–602 (1956).

For certain applications of the novel phenols of the present invention, it is desirable that there be no chlorine in the alkyl side chain of the ω-perfluoroalkyl chloroalkyl phenol. The chlorine is readily removed by dehydrogenation with a base such as for example, sodium hydroxide, to form a ω-perfluoroalkyl alkenyl phenol and this compound can be hydrogenated to give the corresponding ω-perfluoroalkyl alkyl phenol. Also, ω-perfluoroalkyl alkyl phenols may be prepared by performing the dehydrochlorination and hydrogenation as in Example 6.

EXAMPLE 6

An electrically heated rocking autoclave of 250 ml. capacity was charged with 30 grams of 4-methyl-2-(2'-chloro-3'-perfluorooctyl)-n-propyl phenol (0.05 moles), 8.0 grams of potassium hydroxide, 10 ml. of water, 60 ml. of absolute alcohol and 6.0 grams of Raney nickel catalyst. Hydrogen was introduced at 3000 p.s.a. pressure and the autoclave was rocked for four hours while heating at 150° C. At the end of 4 hours the autoclave was cooled to about 50° C., flushed with nitrogen and opened. The contents were removed and cautiously filtered hot (avoiding spontaneous ignition of the catalyst by keeping it wet at all times), and the catalyst was washed with several 50 ml. portions of hot ethanol. The combined filtrate and washings were stirred into about 250 ml. of water and acidified with dilute hydrochlorid acid. The oily layer was separated and purified by absorption on silica gel in a column and elution with a benzene/hexane solvent. After vacuum distillation of the solvent there was obtained about 28 grams of 4-methyl-2-(3'-perfluorooctyl)-n-propyl phenol.

In like manner other ω-perfluoroalkyl-alkyl phenols may be prepared from the corresponding ω-perfluoroalkylchloroalkyl-phenols, including those given in Table III.

The aldehyde condensation products of this invention may be prepared by the reaction of the perfluoroalkyl phenols disclosed above with aldehydes by well known procedures and in accordance with the following examples.

EXAMPLE 7

Into a 500-ml. 3-neck resin flask equipped with mechanical stirrer, reflux column and thermometer, was placed 100 ml. toluene, 294.3 grams (0.50 moles.) of 2-(2'-chloro-3'-perfluorooctyl)-n-propyl phenol, 15.0 grams (0.50 moles) of paraformaldehyde and 30 grams of trichloroacetic acid. The mixture was stirred and heated at 80° to 85° C. for 3 hours and then at reflux (110° C.) for an additional 2 hours. The solution was cooled to about 50° C., 40 ml. of conc. aqueous ammonia was added, and heat applied to reflux the mixture for an additional hour. The reaction mixture was cooled, washed several times with an equal volume of water, and the solvent removed by vacuum distillation taking care to avoid foaming as the material becomes concentrated.

The condensation product, a novolak, as made in the quantity of this example has a molecular weight by vapor phase osmometry of 1000±100. It is a light yellow soft butter-like wax useful for the preparation of compositions having value in the treatment of skin and render it repellent to oil and water.

EXAMPLE 8

Example 7 was repeated with the exception that 0.05 grams of p-toluenesulfonic acid was used as the condensation catalyst in place of 30 grams of trichloroacetic acid. A novolak was obtained that had a molecular weight by vapor phase osmometry of 1650. It was a tan-colored hard wax.

EXAMPLE 9

Into a 500 ml. 3-neck resin flask equipped with a mechanical stirrer, reflux condenser and thermometer were placed 294.3 grams (0.50 moles) of 2-(2'-chloro, 3'-perfluorooctyl)-n-propyl phenol and 55 grams of formaldehyde (30% solution) (0.55 moles). The mixture was stirred and heated to 60° C. and made alkaline to phenolphthalein by dropwise addition of 20% sodium hydroxide in water. The mixture was then heated to 90° C. and stirred at this temperature for 4 hours. After this time, the mixture was cooled to 60° C. and acidified (pH: 6.0) with dilute phosphoric acid. The layers were allowed to separate and the yellow viscous lower layer removed from the flask. After drying in vacuum, a waxy yellow resin was obtained. This material is a resol and useful in further condensations to useful polymeric material. It is also useful for the preparation of protective compositions for the treatment of skin and leather.

EXAMPLE 10

Table IV presents the repellency and substantive properties of a number of fluoroaliphatic phenols and condensation products. It may be observed that, in general, monophenols and compounds with more than one OH per carbocyclic ring exhibit only fair oil and detergent repellency on pigskin and are of less substantivity, i.e., little oil and detergent repellency remains after a detergent wash. Fluoroaliphatic phenol aldehyde condensation products having an average molecular weight of about 900 to about 1600 show good oil and water repellency on pigskin which is very similar to human skin and has the same properties for purposes of testing repellency. They also are substantive to the pigskin as is indicated by the fact that pigskins treated with these condensation products maintain their repellency after a 1-hour wash in a hot detergent solution.

TABLE IV

Properties of Fluoroaliphatic Phenols and Condensation Products

| | Fluoroaliphatic Phenol | Formaldehyde (Condensation Catalyst) | Molecular Weight[a] | Repellency[e] Water | Oil | Substantivity[f] |
|---|---|---|---|---|---|---|
| 1. | OH-C6H3-CH2-CHCl-CH2-C8F17 | CH2O[b] | 1100 | Good | Good | Good |
| 2. | OH-C6H3-CH2-CHCl-CH2-C8F17 | CH2O[c] | 1650 | Good | Good | Poor |
| 3. | OH-C6H3-CH2-CHCl-CH2-C8F17 | CH2O[c] | 790 | Good | Good | Good |

TABLE IV-continued

Properties of Fluoroaliphatic Phenols and Condensation Products

| Fluoroaliphatic Phenol | Formaldehyde (Condensation Catalyst) | Molecular Weight[a] | Repellency[e] Water | Oil | Substantivity[f] |
|---|---|---|---|---|---|
| 4. [structure: phenol with OH, CH₂—CHCl—CH₂, C₈F₁₇] | CH₂O[b] | 2500 | Good | Good | Poor |
| 5. [structure: phenol with OH, CH₂—CHCl—CH₂, C₈F₁₇] | CH₂O[b] | 980 | Good | Good | Fair |
| 6. [structure: chlorophenol with OH, Cl, OSO₂C₈F₁₇] | CH₂O[b] | 1150 | Good | Good | Fair |
| 7. [structure: bisphenol with CH₂—CHCl—CH₂—C₈F₁₇ on both sides, CH₃ groups, bridging CH₂] | | 1218 | Good | Good | Good |
| 8. [structure: phenol with OH, CH₂—CHCl—CH₂, C₈F₁₇] | CH₂O[c] | >3000 | Fair | Fair | Poor |

[a]Molecular weight determined by vapor phase osmometry.
[b]Condensation catalyst is trichloroacetic acid.
[c]Condensation catalyst is p-toluenesulfonic acid.
[d]Test on the dihydroxy-diphenyl methane.
[e]After application of an 8% solution to raw pigskin that had been extracted with tetrahydrofurane, dried, and rehydrated to a flexible condition.
[f]Repellency of treated pigskin after it has been given a 1-hour wash with a 0.5% aqueous solution of sodium dodecylbenzene sulfonate at 40° C.

If the perfluorooctyl group of the compounds and products of Table IV are replaced by other perfluoro groups including perfluorobutyl, perfluoroamyl, perfluorohexyl, perfluorododecyl, perfluoroodecyl, and other perfluoroalkyl groups, corresponding compounds and products are obtained that have properties similar to those listed in Table IV.

If the formaldehyde used in the condensation products of Table IV is replaced by other aldehydes including acetaldehyde, benzaldehyde, butyraldehyde, furfuraldehyde, glutaraldehyde, glyoxal, paraldehyde, propionaldehyde, tetrahydrofurfuraldehyde, and other aldehydes desirable condensation products are also obtained that have properties similar to those listed in Table IV.

The following example demonstrates a preferred application of the condensation products of this invention in a composition that provides effective protection of the skin against aqueous and oily material that otherwise might injure the skin.

EXAMPLE 11

To prepare a perfumed protective handcream, an aqueous solution of 82.35 parts of water, 0.3 parts of ammonium lauryl sulfate, and 0.15 parts of Tegosept M (methyl ester of p-hydroxybenzoic acid, a water soluble bactericide) was heated to 50° C. and added to a high shear mixer (Homomixer). An oil phase solution of 3.0 parts of cetyl alcohol, 4.0 parts of the novolak of 2-(2'-chloro-3'-perfluorooctyl)-n-propyl phenol (prepared as described in Example 7), 0.10 parts of Tegosept P (propyl ester of p-hydroxybenzoic acid, an oil soluble bactericide) and 0.004 parts of propyl gallate (antioxidant) was also heated to 50° C. was slowly added to the aqueous mixture, the entire mixture was thoroughly mixed and while mixing, cooled to 32° C., then 0.10 parts of perfume "Flueroma Fragrance No. 9006" available from U.O.P. Fragrances Division of Universal Oil Products, Inc., New York, was added. After the creamy emulsion is cooled to below about 30° C. while mixing, it is discharged from the mixer.

The emulsion was then rubbed onto the hands in the usual manner and was found to be protective against water, oil and detergents.

Handcreams with similar desirable properties may be prepared by using in accordance with Example 11 from 0.5 to 4 parts of cetyl alcohol per 100 parts of handcream. Less cetyl alcohol than 0.5 parts gives thin unstable emulsions and more than 4 parts of cetyl alcohol reduces the oil repellency of the handcream. Likewise, the preferred concentration of perfume or fragrance depends on the type of fragrance used. In general, a useful concentration is from about 0.05 parts up to 0.15 parts per 100 parts of handcream. Less than 0.05 parts of fragrance is ineffective and more than 0.15 may reduce the oil repellency of the handcream. Also, handcreams with desirable properties may be prepared by using in accordance with Example 4 from 0.2 to about 0.4 parts of ammonium lauryl sulfate.

The cream of Example 11 was the result of the study of many formulations to find composites that do not have components that interfere with the substantivity of condensation products of the invention. In general, inorganic thickeners, fugitive surfactants, fluorochemical surfactants, fatty acids, most common surfactants and most fatty alcohols are to be avoided because rather large quantities of these materials are required to achieve emulsion stability. At the high concentration of these materials required the substantivity and repellency of the condensation products of this invention are reduced.

EXAMPLE 12 lauryl sulfonate at 45° C., rinsed with warm water and dried.

It may be seen by inspection of Table V that the creams and lotions made using novolaks of 2-(2'-chloro-3'-perfluorooctyl)-n-propyl phenol exhibit oil and soap repellency and that this condensation product is substantive to callus tissue. These results are indicated by the high contact angle of drops of oil on treated callus tissue after it has been washed in hot detergent solution. Creams and lotions made with other novolaks and aldehyde condensation products having an average molecular weight of from about 900 to about 1600 in accordance with the teaching of this invention are repellent to aqueous and oily substances and are substantive to skin and proteinaceous materials.

TABLE V

Repellency Tests on Callus Tissue

| | Droplet Contact Angle | | | | | | | |
|---|---|---|---|---|---|---|---|---|
| | Before Detergent Wash | | | | | After Detergent Wash | | |
| Elapsed Time | Untreated | | Preparation of Example 11 | | Preparation of Example 12 | | Preparation of Example 11 | Preparation of Example 12 |
| Seconds | Oil | Soap | Oil | Soap | Oil | Soap | Untreated | Oil | Oil |
| 2 | 28° | 76° | 89° | 97° | 84° | 101° | <10° | 78° | 75° |
| 15 | 20° | 51° | 82° | 96° | 82° | 99° | wets out | 74° | 72° |
| 30 | 15° | 43° | 80° | 93° | 78° | 96° | almost | 70° | 68° |
| 60 | <10° | 27° | 78° | 93° | 76° | 95° | immediately | 63° | 64° |
| 300 | <10° | <10° | 76° | 72° | 75° | 84° | | 47° | 52° |

A protective lotion was prepared by dissolving 0.004 parts of propyl gallate, 4 parts of the novolak of 2-(2'-chloro-3'-perfluorooctyl)-n-propyl phenol (prepared as in Example 1) and 0.1 part of perfume in 96 parts of denatured ethyl alcohol. The resulting lotion provided protection of the hands against hot soapy water. When applied to the hands and other parts of the body, the cream provided protection against aqueous and oily solutions. In place of denatured ethyl alcohol, isopropanol or a Freon or a mixture of one of more Freons having a boiling point of about 70° to about 150° F. may be used. If the lotion is to be used to treat leather, textiles, or synthetic materials, then other solvents may be used including diethyl ether, acetone, methyl ethyl ketone, amyl acetate, benzene, chlorinated hydrocarbons and the like.

EXAMPLE 13

The repellency and substantive properties of the protective compositions of this invention were determined by photographically measuring droplet contact angles over a five minute period. Pigskin or callus tissue was treated with the test formulation as prepared in Example 11, permitted to dry after which a droplet of soap solution (0.5% sodium lauryl sulfonate in deionized water) or oil (75% mineral oil of 310 to 320 Saybolt-seconds in heptane) was placed on the surface from a syringe. Pictures taken level with the treated surface at times of 0, 15, 30, 60 and 300 seconds were used to determine the wetting rates of these potential irritants. Initial contact angle as well as rate of change of contact angles were used to compare repellencies of formulations. Substantivity is measured by determining the contact angle of the mineral oil-heptane mixture on the treated callus tissue or pigskin after it is subjected to a 40 minute wash with a 0.5% solution of sodium

EXAMPLE 14

An aerosol spray embodying the compositions of the invention is prepared by charging a 6 ounce aerosol can with 90 rams of a 4% solution of the novolak of 2-(2'-chloro-3'-perfluorooctyl)-n-propyl phenol (prepared as in Example 7) in ethanol and 90 grams of a 40:60 mixture of Freon 11 and Freon 12. To disperse the protective composition, the aerosol can is equipped with a "Precision" valve and dip tube. When sprayed on the hands or other parts of the body, a pleasant emollient character is noted and the hands and body are afforded protection against oil and aqueous based irritants, acid and basic solutions even after the hands and body are washed in water or detergent solutions.

What is claimed is:

1. A compound having the formula $$\underset{R_2\quad R_3\quad R_4}{\underset{}{\text{OH}}}\text{CH}_2XR_f$$

wherein X is —CHClCH$_2$—, —CH=CH—, or —CH$_2$—CH$_2$—; R$_f$ is a perfluoroalkyl having from 3 to 20 carbon atoms; $R_1$, $R_2$, $R_3$, and $R_4$ are selected from the class consisting of methyl, ethyl, methoxy, phenyl, phenoxy, hydrogen, and halogen and $R_1$ and $R_3$ can be —$CH_2XR_f$.

2. The compound

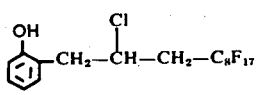

according to claim 1.

3. A compound of claim 1 comprising a mixture of

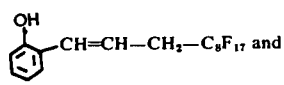 and 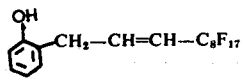

4. The compound

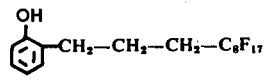

according to claim 1.

5. The compound

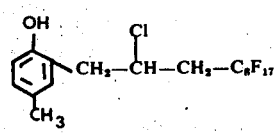

according to claim 1.

6. A compound having the formula

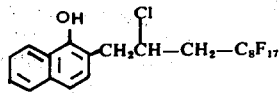

7. A compound having the formula

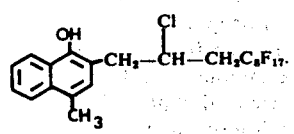

* * * * *